United States Patent [19]

Siedel et al.

[11] Patent Number: 4,727,025
[45] Date of Patent: Feb. 23, 1988

[54] PROCESS AND REAGENT FOR THE FULLY ENZYMATIC DETERMINATION OF UREA

[75] Inventors: Joachim Siedel, Bernried; August W. Wahlefeld, Hohenpeissenberg; Joachim Ziegenhorn, Starnberg, all of Fed. Rep. of Germany

[73] Assignee: Boehringer Mannheim GmbH, Mannheim-Waldhof, Fed. Rep. of Germany

[21] Appl. No.: 823,489

[22] PCT Filed: May 23, 1985

[86] PCT No.: PCT/EP85/00250

§ 371 Date: Jan. 10, 1986

§ 102(e) Date: Jan. 10, 1986

[87] PCT Pub. No.: WO85/05641

PCT Pub. Date: Dec. 19, 1985

[30] Foreign Application Priority Data

May 25, 1984 [DE] Fed. Rep. of Germany ....... 3419642

[51] Int. Cl.⁴ .............................................. C12Q 1/58
[52] U.S. Cl. ......................................... 435/12; 435/15
[58] Field of Search ............................................ 435/12

[56] References Cited

U.S. PATENT DOCUMENTS 4,465,770  8/1984  Modrovich ..................... 435/12

FOREIGN PATENT DOCUMENTS 3247894  6/1984  Fed. Rep. of Germany.

OTHER PUBLICATIONS

Trijbels et al.—Chem. Abst., vol. 66, (1967), p. 43898d.
Vander Drift et al.—Chem. Abst., vol. 75, (1971), p. 84644x.

Primary Examiner—Sam Rosen
Attorney, Agent, or Firm—Felfe & Lynch

[57] ABSTRACT

For the enzymatic determination of urea, one reacts the urea with glyoxylate in the presence of ureidoglycolate synthetase to give (S)-ureidoglycolate and oxidizes the latter with NAD(P)+ and ureidoglycolate dehydrogenase to carbamoyloxamate and measures NAD(P)H formed either directly or via a color indicator system. A reagent suitable herefor contains glyoxylate, NAD(P)+, (S)-ureidoglycolate synthetase, ureidoglycolate dehydrogenase and buffer substance.

12 Claims, 1 Drawing Figure

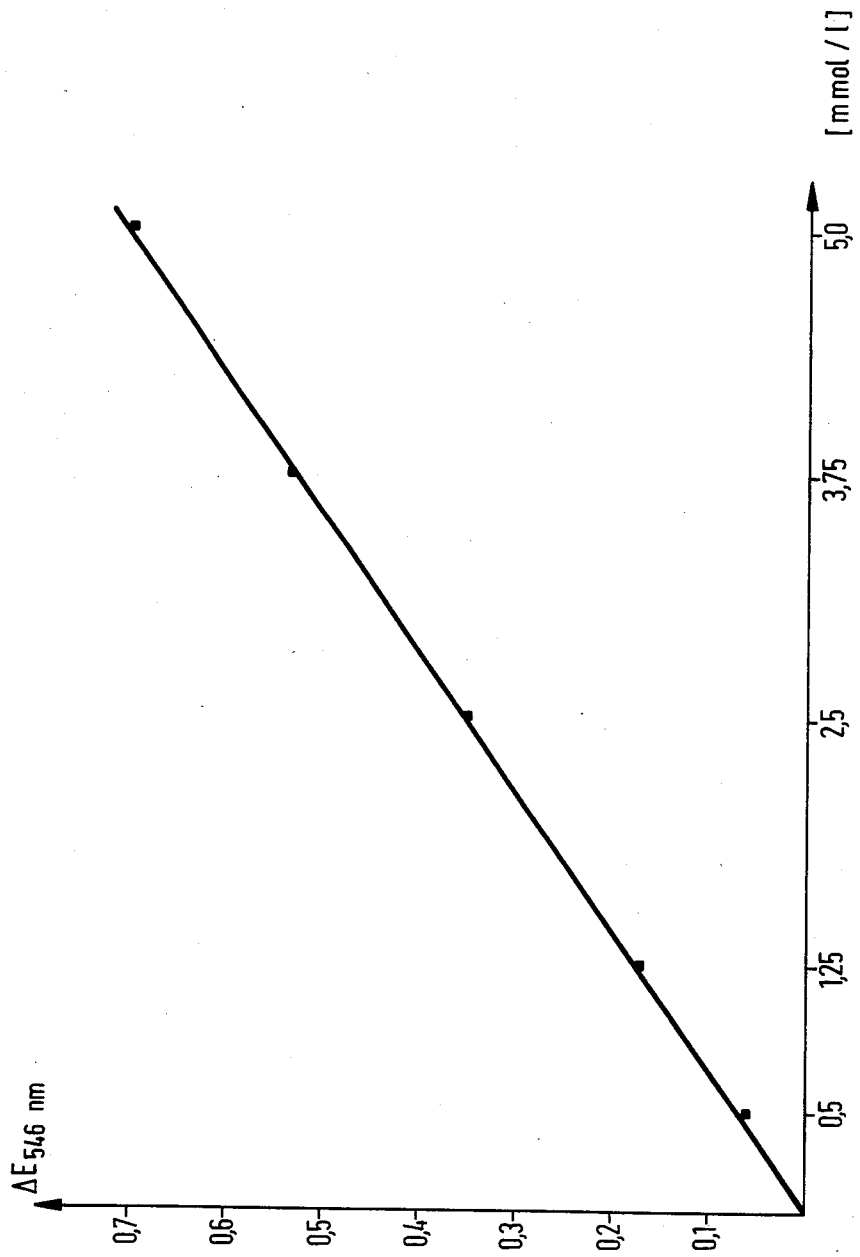

PROCESS AND REAGENT FOR THE FULLY ENZYMATIC DETERMINATION OF UREA

DESCRIPTION

The invention concerns a process and reagent for the enzymatic determination of urea, especially in body fluids, such as serum, plasma and urine.

Within the scope of analytical chemistry, the quantitative determination of urea plays an especially important part in clinical-chemical diagnosis. The urea concentration in body fluids, such as serum or urine, gives the clinical physician important indications regarding the kidney function, furthermore in the case of dialysis patients regarding the degree of action of extra- and intracorporeal blood washing.

In comparison with purely chemical or partly enzymatic photometric determination processes (e.g. the methods used especially frequently with the use of Fearon's reagent or of the urease/Berthelot reaction (for the description see e.g. R. J. Henry, D. C. Cannon, J. W. Winkelmann (eds.), Clinical Chemistry: Principles and Techniques, 2nd edition, Harper and Row; Hagerstown, Md., U.S.A. (1974), pages 503–526), fully enzymatic analysis methods achieve more and more importance. Their important advantages, in comparison with the above-mentioned processes, are the high specificity, their nm-disturbance, e.g. towards medicament influences, temperatures and pH variations, the avoidance of the use of corrosive, strongly acidic or alkaline or toxic reagents, their universal usability not only for the manual carrying out of the test but also on the most varied automatic analysers, as well as the possibility to be able to evaluate the measurement results, without the concurrent use of standards, with the help of precisely defined conversion factors, whereby the conditions of the Lambert-Beer Law are, in principle, ensured over the whole extinction range usable on the photometer.

Hitherto, two different processes have been known for the fully enzymatic urea determination.

In one of these processes, urea is split hydrolytically with urease E.C. 3.5.1.5 into two molecules of ammonia and one molecule of $CO_2$; from the resultant ammonia, there is formed glutamate in the presence of α-ketoglutarate, NADH and glutamate dehydrogenase E.C. 1.4.1.3. The decrease of the NADH concentration in the reaction mixture, which can be measured photometrically at 334, 340 or 365 nm, is proportional to the amount of urea used (H. U. Bergmeyer (ed.), Methoden der enzymatischen Analyse, 3rd edition, Vol. II, Verlag Chemie, Weinheim (1974), p. 1842). According to the second process (U.S. Pat. No. 3,655,516), urea is hydrolysed in an ATP-dependent reaction by means of urea amidohydrolase E.C. 6.3.4.6, whereby one molecule of ADP is formed per mole of reacted urea. This is converted back into ATP with phosphoenol pyruvate and pyruvate kinase E.C. 2.7.1.40 and the liberated pyruvate is reduced to lactate in the presence of NADH and lactate dehydrogenase E.C. 1.1.1.27. As in the first-mentioned process, the measurement parameter is here also the decrease of the NADH concentration in the reaction mixture.

Of the two processes, up to today, only the first has found wide use in routine analysis.

In spite of the marked advantage which the fully enzymatic determination of urea has provided in comparison with the purely chemical or partly enzymatic methods of analysis, nevertheless both the abovementioned enzymatic processes display several substantially identical disadvantages: On the one hand, NADH is relatively unstable in aqueous solution, even in the neutral pH range, so that the storage stability of the reagent solutions ready for use is only ensured for a comparatively short period of time, i.e. about 1 day at room temperature or 3 days in the case of storage at 2° to 8° C. Furthermore, test batches according to the sample/reagent blank measurement process sometimes give rise to falsely increased urea values if it is necessary to work with sample materials which are turbid or absorb strongly in the range of 334 to 365 or if comparatively high concentrations are present of ammonia or pyruvate which are always present in traces in serum or urine. Thus, for exact urea determinations, it is here necessary to carry out a separate sample blank batch (reagent without urease or urea amidohydrolase) which considerably complicates at least the manual carrying out of the test. Admittedly such disturbances can, in principle, be excluded by the use of kinetic measurement techniques which, however, can only be carried out with sufficient precision on automatic analysers and, on the other hand, substantially exclude the manual carrying out of the test.

Finally, in both cases, because of the properties of the indicator reaction, no possibility is provided to couple on a colour-providing visualisation system which, on the one hand, would substantially exclude disturbances due to sample turbidities or inherent colorations and, furthermore, permit the use of photometers measuring in the visible range which do not possess any devices for measurement in the UV range.

Therefore, there is a need for a fully enzymatic process and reagent for the specific determination of urea which avoids the above-mentioned disadvantages, i.e. strictly limited storage stability of the analysis reagent, as well as simultaneous detection of disturbing sample components, and also makes possible the carrying out of the measurement in the visible wavelength range.

According to the invention, this task is solved by a process for the enzymatic determination of urea which is characterised in that one reacts urea with glyoxalate in the presence of (S)-ureidoglycolate synthetase to give (S)-ureidoglycolate and oxidises the latter with $NAD^+$ or $NADP^+$, preferably with $NAD^+$, as well as ureidoglycolate dehydrogenase, E.C.1.1.1.154, with stoichiometric formation of NADH or NADPH, to give carbamoyloxamate.

The concentration determination of urea can take place either directly, i.e. via the measurement of the NADH or NADPH formed between 334 and 365 nm, or preferably via an NAD(P)H-dependent enzymatic colour indicator system.

Especially preferred is a system in which, from NADH or NADPH, in concentration-dependent manner, there is formed a formazan coloured material from a tetrazolium salt in the presence of diaphorase, E.C. 1.6.4.3.

The enzyme reactions forming the basis of the process (ureidoglycolate synthetase or ureidoglycolate dehydrogenase reaction) have admittedly been known for almost 20 years from J. Bacteriology, Vol. 90, p. 1531–1536 (1965). However, it is there taught that the ureidoglycolate synthesis takes place extraordinarily slowly and in the case of, in each case, 20 μm. urea and glyoxylate, after 1 hour only 10% had reacted. It is, therefore, surprising that the determination according to the invention can, nevertheless, be carried out.

(S)-ureidoglycolate synthetase can be obtained with sufficient purity and activity according to the process described in J. Bacteriology, 90, 1525-1530 (1965). The occurrence of the enzyme has already been described for many micro-organisms, such as e.g. *Saccharomyces cerevisiae, Candida utilise* and Streptococci. *Streptococcus allantoicus*, DSM 2965, is preferred as starting material.

A further subject of the invention is a reagent for the determination of urea which is characterised in that it consists of an aqueous, buffered solution which contains glyoxylate, $NAD^+$ or $NADP^+$, (S)-ureidoglycolate synthetase and ureidoglycolate dehydrogenase, as well as preferably an NAD(P)H-dependent colour indicator system. Especially preferred is a reagent which additionally contains, as NAD(P)H-dependent colour indicator system, diaphorase and a tetrazolium salt reductively convertible into a formazan coloured material.

The pH value of the aqueous solution expediently lies between 7 and 9, preferably between 7.5 and 8.5, quite especially preferably between 7.7 and 8.3. For the adjustment of the pH value, there come into question all buffer substances, the pK values of which lie between pH 6.5 and 9.5. Phosphate and tris buffer are especially suitable. The concentration of buffer substance expediently amounts to 20 to 200 mmol/l., preferably 50 to 150 mmol/l. For glyoxylate, there come into question concentrations of 0.1 to 10 mmol/l, preferably 0.5 to 5 mmol/l., quite especially preferred 1 to 3 mmol/l. Of the co-enzymes $NAD^+$ and $NADP^+$, $NAD^+$ is preferred; the concentration of the co-enzyme favourably lies between 1 to 20 mmol/l., preferably at 5 to 10 mmol/l. For (S)-ureidoglycolate synthetase, concentrations of 1 to 30 U/ml. are expedient, preferably 3 to 20 U/ml., especially preferably 5 to 10 U/ml. The same also applies to ureidoglycolate dehydrogenase.

The diaphorase concentration normally lies between 0.1 and 10 U/ml., preferably between 0.5 and 5 U/ml., especially preferably between 1 and 2 U/ml. Of the tetrazolium salts, 3-(4',5'-dimethylthiazol-2-yl)-2,4-diphenyltetrazolium bromide (MTT) and 2,2'-di-(p-nitrophenyl)-5,5'-diphenyl-3,3'-(3,3'-dimethoxy-4,4'-diphenylene)-ditetrazolium chloride (NBT) are preferred, especially NBT. Examples of other suitable tetrazolium salts are INT (2-(p-iodophenyl)-3-(p-nitrophenyl)-5-phenyltetrazolium chloride), TNBT (2,2',5,5'-tetra(p-nitrophenyl)-3,3'-(3-dimethoxy-4-diphenylene)ditetrazolium chloride), NT (2,2'-p-diphenylene-3,3',5,5'-tetraphenylditetrazolium chloride) and TT (2,3,5-triphenyltetrazolium chloride). Their concentrations in the reagent usually lie between 0.05 and 1 mmol/l., preferably between 0.1 and 0.5 mmol/l. In order to prevent a premature precipitating out of the formazan formed, to the reagent there is preferably also added a non-ionic detergent, such as e.g. Triton X-100, namely, in a concentration of 0.1 to 0.5%, especially of 0.2 to 0.4%.

BRIEF DESCRIPTION OF THE DRAWING

FIG. 1 shows the dependence of ΔE against the concentration of urea in the sample.

The following Example further explains the invention:

EXAMPLE 1

Reagent and process for the determination of urea.

(A) For the preparation of ureidoglycolate dehydrogenase, *Proteus rettgeri*, DSM 2964, was cultured aerobically in a medium of 10 g. Difco yeast extract, 7 g. allantoin, 0.18 g. $MgSO_4.7H_2O$/l. of tap water, the biomass centrifuged off and digested by ultrasonics in 0.05 mol/l. tris.HCl, pH 7.0. For the enzyme purification, the crude extract was fractionated over polyethyleneimine G 35 and subsequently chromatographed over phenyl-Sepharose, then subjected to a first ammonium sulphate fractionation, to a chromatography on Sepharose S-200 and finally to a second AS fractionation. The purified enzyme displays a specific activity of 144 U/mg. protein and was stored as suspension in 3.2 mol/l. AS, pH 8.1, with a concentration of 5 mg./ml.

Before use for the determination of urea, it is recommended to remove the ammonium sulphate from the enzyme preparation by dialysis against 0.1 mol/l. tris. HCl.

(B) Colour reagent

| components | concentration in the reagent |
| --- | --- |
| tris.HCl (pH 8.0) | 100 mmol/l. |
| Triton X-100 | 0.3% |
| Na glyoxylate | 3 mmol/l. |
| $NAD^+$ | 5 mmol/l. |
| NBT | 0.2 mmol/l. |
| (S)—ureidoglycolate synthetase | 10 U/ml. |
| ureidoglycolate dehydrogenase | 7 U/ml. |
| diaphorase | 1 U/ml. |

(C) Test carrying out

Wavelength 546 nm, T=25° C., layer thickness 10 mm.

Measurement against reagent blank.

Into a cuvette pipette:

| | sample value (S) | reagent blank+ (RB) |
| --- | --- | --- |
| colour reagent 1.1 | 1.00 ml. | 1.00 ml. |
| sample++ | 0.01 ml. | — | mix, incubate for 20 minutes at 25° C., then, within a further 30 minutes, measure $E_S$ against $E_{RB}$ (Δ E).

+Per measurement series, the batch of one reagent blank suffices.
++aqueous solutions of urea with concentrations of 0.5 to 5 mmol/l.

We claim:

1. Process for the enzymatic determination of urea, comprising reacting a urea containing sample with glyoxylate in the presence of (S)-ureidoglycolate synthetase to form (S)-ureidoglycolate, oxidizing the (S)-ureidoglycolate with $NAD(P)^+$ and ureidoglycolate dehydrogenase to form carbamoyloxamate and NAD(P)H and measuring NAD(P)H formed as a measure of urea in said sample.

2. The process of claim 1, wherein the NAD(P)H is measured with a color indicator system and the measuring comprises reacting the NAD(P)H with a tetrazolium salt in the presence of diaphorase to give a formazan coloured material and measuring said material.

3. The process of claim 1 wherein the ureidoglycolate dehydrogenase is from *Proteus rettgeri*, DSM 2964.

4. A reagent for the enzymatic determination of urea, comprising glyoxylate, $NAD(P)^+$, (S)-ureidoglycolate synthetase, ureidoglycolate dehydrogenase and a buffer substance.

5. The reagent of claim 4, further comprising a color indication system for determining NAD(P)H and which includes diaphorase and tetrazolium salt.

6. The reagent of claim 5 in the form of an aqueous solution, and containing 0.1 to 10 mmol/l. glyoxylate, 1 to 20 mmol/l. NAD(P)+, 1 to 30 U/ml. each of (S)-ureidoglycolate synthetase and ureidoglycolate dehydrogenase, 0.1 to 10 U/ml. diaphorase, 0.05 to 1 mmol/l. tetrazolium salt and 20 to 200 mml/l. buffer substance pH 7 to 9.

7. The reagent of claim 6, containing 0.5 to 5 mmol/l. glyoxylate, 5 to 10 mmol/l. NAD(P)+, 3 to 30 U/ml. each of (S)-ureidoglycolate synthetase and ureidoglycolate dehydrogenase, 0.05 to 5 U/ml. diaphorase and 0.1 to 0.5 mmol/l. tetrazolium salt and 50 to 150 mmol/l. buffer substance of pH 7.5 to 8.5.

8. The reagent of claim 7 further containing 0.1 to 0.5 wt.% of a non-ionic detergent.

9. The reagent of claim 4 wherein said buffer is a phosphate buffer or tris buffer.

10. The reagent of claim 5 wherein said tetrazolium salt is 3-(4',5'-dimethylthiazol-2-yl)-2,4-diphenyltetrazolium bromide (MTT) or 2,2'-di-(p-nitrophenyl)-5,5'-diphenyl-3,3'-(3,3'-dimethoxy-4,4'-diphenylene)-ditetrazolium chloride (NBT).

11. The reagent of claim 6 further comprising 0.1 to 0.5 wt.% of a non-ionic detergent.

12. The reagent of claim 6 wherein said buffer is a phosphate buffer or a tris buffer.

* * * * *

UNITED STATES PATENT AND TRADEMARK OFFICE
CERTIFICATE OF CORRECTION

PATENT NO. : 4,727,025
DATED : February 23, 1988
INVENTOR(S) : Joachim Siedel, et al.

It is certified that error appears in the above-identified patent and that said Letters Patent is hereby corrected as shown below:

Claim 7, line 4, change "0.05" to -- 0.5 --.

Signed and Sealed this

Eighth Day of November, 1988

Attest:

DONALD J. QUIGG

Attesting Officer

Commissioner of Patents and Trademarks